United States Patent [19]

Therriault et al.

[11] Patent Number: 4,863,449
[45] Date of Patent: Sep. 5, 1989

[54] ADHESIVE-LINED ELASTIC CONDOM CATHETHER

[75] Inventors: Donald J. Therriault, York, Pa.; Robert G. Olach, Crystal Lake; John S. Biersteker, Prospect Heights, both of Ill.

[73] Assignee: Hollister Incorporated, Libertyville, Ill.

[21] Appl. No.: 191,069

[22] Filed: May 6, 1988

Related U.S. Application Data

[62] Division of Ser. No. 70,171, Jul. 6, 1987, Pat. No. 4,769,099.

[51] Int. Cl.⁴ ............................................. A61F 5/44
[52] U.S. Cl. ..................... 604/352; 128/844
[58] Field of Search .................. 604/349–353, 604/389; 428/343, 352, 354, 355, 212; 128/842, 844

[56] References Cited

U.S. PATENT DOCUMENTS

| 2,389,831 | 11/1945 | Welsh | 604/352 |
| 2,822,290 | 2/1958 | Webber | 428/352 |
| 3,403,682 | 10/1968 | McDonell | 604/352 |
| 4,475,910 | 10/1984 | Conway et al. | 604/349 |

FOREIGN PATENT DOCUMENTS 8600816  2/1986  World Int. Prop. O. ......... 604/349

Primary Examiner—Jerome L. Kruter
Attorney, Agent, or Firm—Tilton, Fallon & Lungmus

[57] ABSTRACT

A tubular elastic sheath for a condom catheter, the sheath taking the form of a thin, flexible, cylindrical member of elastic material having inner and outer surfaces and being rolled outwardly upon itself to form a torus having successively larger turns. A thin, flexible, multi-layered tape is interposed between successive turns of the rolled torus with such layers, all adhering to each other and to the catheter member, comprising a first adhesive layer, a second adhesive layer, and a highly-stretchable elastomeric layer disposed between the first and second adhesive layers. The first adhesive layer adheres to the inner surface of the catheter member and the second adhesive layer adheres to the outer surface of that member, and the relationship is such that the elastomeric layer adheres more securely to the second adhesive layer than to the first adhesive layer, and the first adhesive layer has less affinity for the elastomeric layer than each of the adhesive layers has for the surfaces of the catheter member. As a result, when the sheath is unrolled, the tape undergoes delamination with the first adhesive layer remaining upon the sheath's inner surface and the second adhesive layer, covered by the elastomeric layer, remaining on the sheath's outer surface.

4 Claims, 3 Drawing Sheets

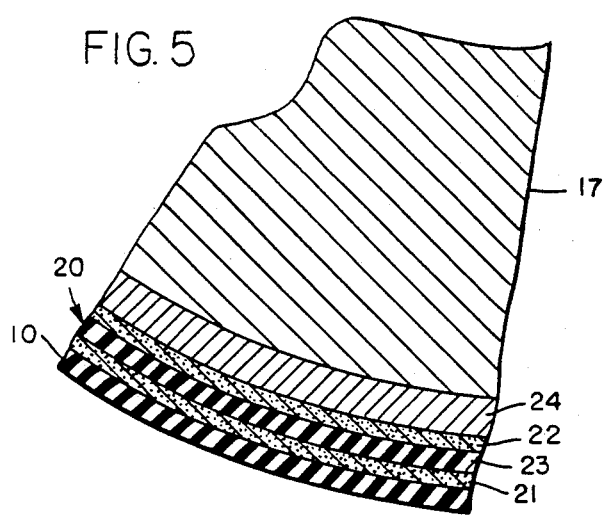
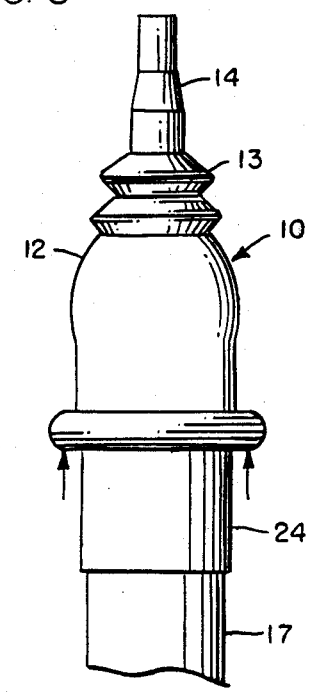
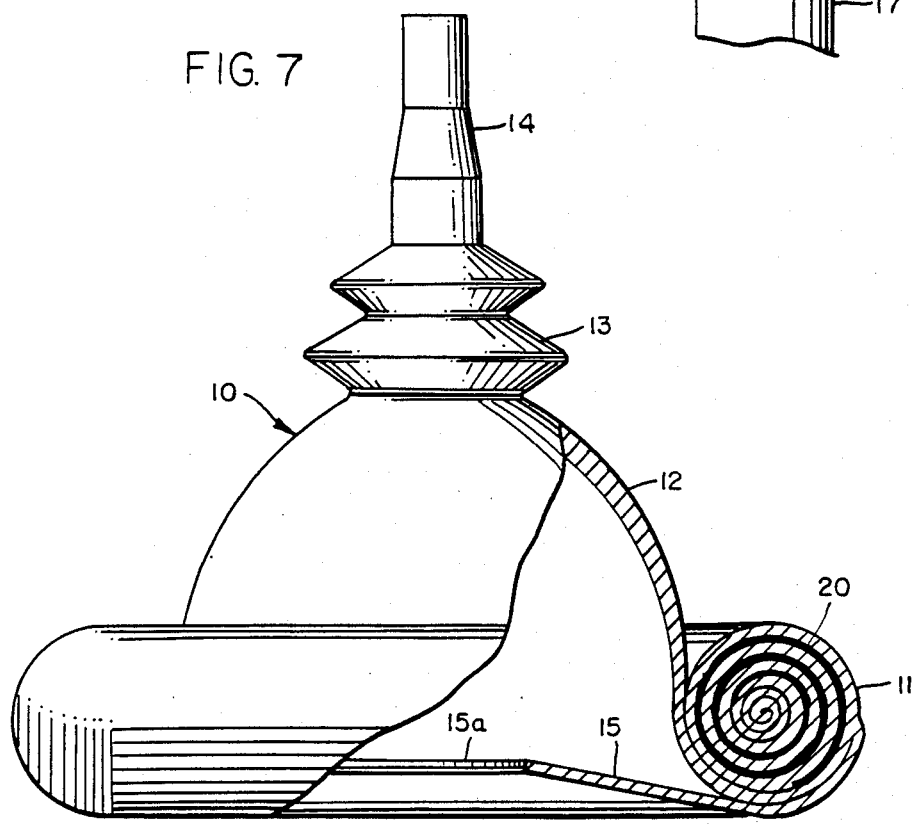

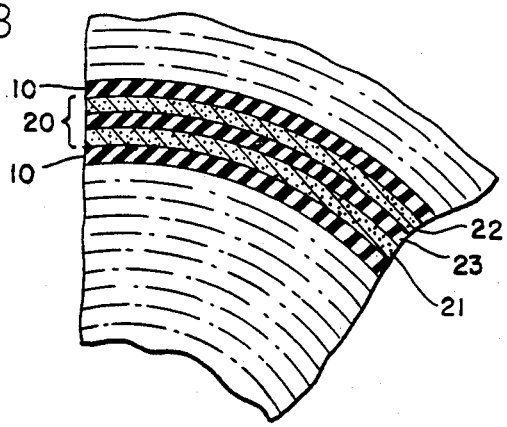
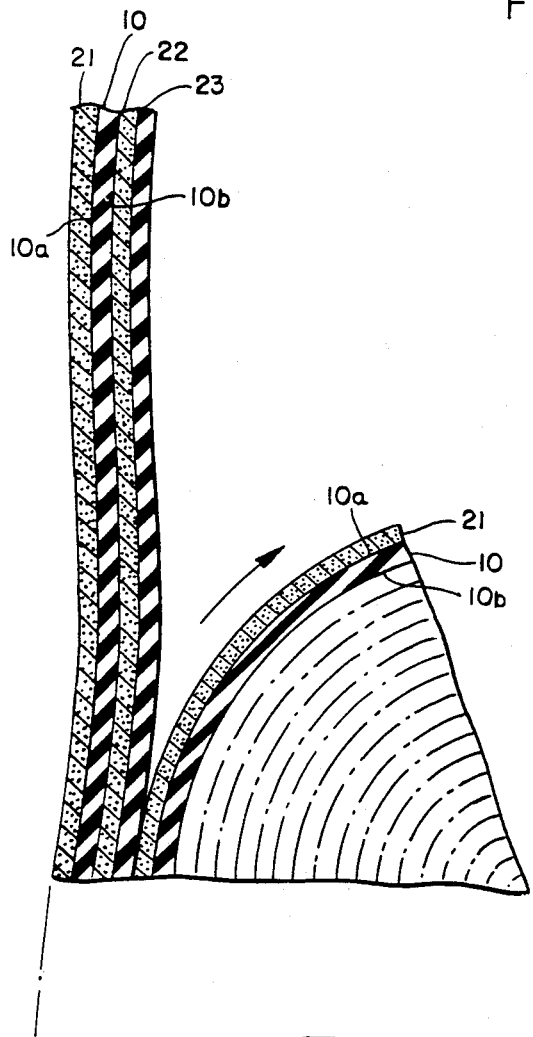
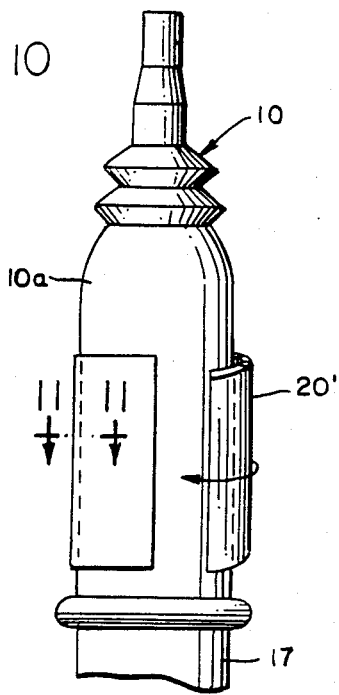
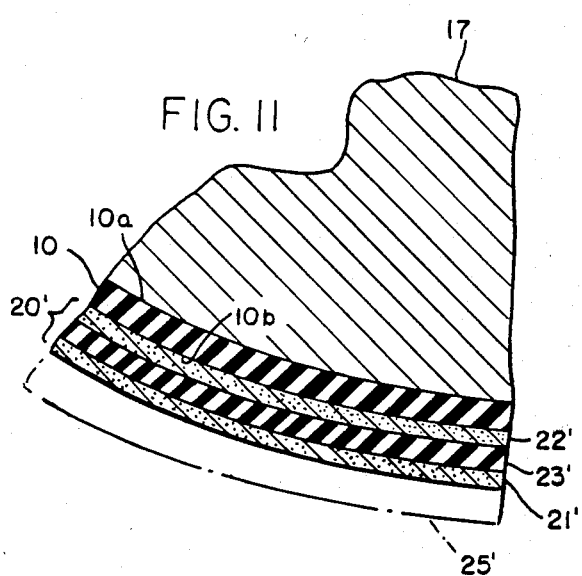

ADHESIVE-LINED ELASTIC CONDOM CATHETHER

This application is a division of application Ser. No. 70,171, filed July 6, 1987 now U.S. Pat. No. 4,769,099.

BACKGROUND OF THE INVENTION

U.S. Pat. No. 4,626,250 depicts, in FIG. 18, a sheath for a male external catheter in which an adhesive coating 50 is disposed along the inner surface of the sheath's cylindrical body for adhesively securing the sheath to the penile shaft of a user. As indicated in FIG. 19, the sheath is supplied to the user in rolled form with the adhesive layer interposed between successive coils or turns and then, as the sheath is unrolled, the adhesive, which remains on the sheath's inner surface, is advanced into contact with the wearer. Effective application of the device obviously requires that the adhesive coating refrain from adhering to the sheath's outer surface as the sheath is unrolled and, as explained in the patent (column 10), any suitable release coating or interliner as well known in the tape industry and in other fields may be used for that purpose. In the example given, a silicone coating is provided on the sheath's outer surface to keep the adhesive 50 from adhering to that surface when the sheath is unrolled.

A common method for providing such a silicone coating during sheath manufacture is by a dipping step since other techniques, such as spraying, provide less control and create other problems in the workplace. Such problems are not entirely avoided even when a dipping process is used, since silicone tends to migrate even under carefully controlled working conditions, causing complications with equipment and silicone exposure to other surfaces not intended to be treated. Furthermore, the silicone baths into which catheter sheaths may be dipped tend to be very sensitive to ambient conditions. For example, under conditions of relatively high humidity, the useful life of such a bath may be greatly reduced, resulting in substantial material waste and increased manufacturing costs. Sheaths treated with silicone that has been adversely affected by humidity may be rendered unusable because the release coatings may not cure properly if at all. Furthermore, even after application and curing, silicone release coatings applied by dipping may prove troublesome, resulting in discoloration, blushing, flaking, cracking, and loss of release properties.

Some of these problems are summarized in International Patent Application PCT/DK85/00068, published February 13, 1986. There, reference is made to the laborious prior art manufacturing procedures that first require forming of a catheter's body portion by immersing a mandrel into a latex solution, followed by rinsing and drying prior to the application of a silicone rubber layer, followed by curing of the silicone rubber layer before application of an adhesive which is then expected to transfer from the silicone rubber layer to the inside surface of the catheter when the product is rolled during the final stage of manufacture and later unrolled at time of use. Reference may also be had to U.S. Pat. No. 4,475,910 for discussion of the adhesive-transfer procedure.

Application PCT/DK85/00068 further discloses a procedure which eliminates the need for a silicone dipping step and thereby avoids many of the problems inherent in such a procedure. Unfortunately, the purported improvement is itself relatively complex, involving the application of an adhesive strip to one surface of the sheath and a silicone-bearing strip to the sheath's opposite surface. Means must be provided for inflating and deflating the sheath during processing in order to bring the strips into contact with the sheath's opposite surfaces at precise locations which will permit the adhesive and release coatings to register properly when the sheath is rolled in the final stage of manufacture.

SUMMARY OF THE INVENTION

An important aspect of this invention therefore lies in overcoming the problems inherent in the conventional application of liquid release coatings and liquid adhesive agents without substituting a procedure that adds further problems, complexities and expenses to the manufacturing operations. Specifically, this invention involves a method in which a single tape is used to apply both an adhesive layer and a release layer to opposite surfaces of a cylindrical elastic sheath without the use of inflating, spraying, drying, curing, or other time-consuming steps commonly associated with prior production techniques. A further aspect of the invention lies in providing not only a superior manufacturing method, but also an improved product. Risks of pinholes in critical areas of a sheath may be appreciably reduced by the method and product of this invention.

Briefly, the method involves the use of a laminated tape having first and second adhesive layers separated by an elastomeric core layer. The elastomeric core layer may be of homogeneous composition, such as silicone rubber, or may itself be composed of at least two sub-layers, one being an elastomeric sub-layer and the other being a release sub-layer. In any event, the elastomeric core layer must have greater affinity for one adhesive layer than for the other adhesive layer. In the manufacturing procedure, one of such adhesive layers, referred to as a "first" layer, is intended for adherence to the sheath's inner surface, whereas the "second" adhesive layer is intended for ultimate adherence to the sheath's outer surface. In such an arrangement, the elastomeric core layer must have greater affinity for the second adhesive layer than for the first adhesive layer. Also, it is essential that the first adhesive layer have less affinity for the elastomeric core layer than either of the adhesive layers have for the surfaces of the sheath.

This means that during manufacture, the laminated tape may be brought into adhesive contact with the catheter sheath when that sheath is in unrolled condition on a supporting mandrel. Such contact may be made either by placing the tape with its first adhesive layer in adhesive contact with the inner surface of the sheath or, alternatively, with its second adhesive layer in contact with the sheath's outer surface. Thereafter, the sheath is rolled upon the mandrel so that the laminated tape is interposed between successive rolls or turns of the sheath with the first adhesive layer in adhesive engagement with the sheath's inner surface and with the tape's second adhesive layer in engagement with the sheath's outer surface. Thereafter, when the sheath is unrolled during application to a wearer, the tape delaminates with the first adhesive layer adhering to the sheath's inner surface, and securing the sheath to the penile shaft, and the second adhesive layer, along with the elastomeric covering layer, adhering to the sheath's outer surface.

Other features, advantages, and objects of the invention will become apparent from the specification and drawings.

DRAWINGS

FIG. 5 is an enlarged fragmentary sectional view taken along line 5—5 of FIG. 4.

FIG. 6 is a fragmentary side elevational view similar to FIGS. 2 and 4 but showing a further step in which the sheath is again rolled upon the mandrel.

FIG. 7 is an enlarged elevational view, shown partly in section, depicting a finished catheter embodying this invention.

FIG. 8 is an enlargement of a section of a rolled portion of the sheath shown in section in FIG. 7 but illustrating in solid lines only certain portions of the roll as described in conjunction with the subsequent peeling or delaminating step.

FIG. 9 is a fragmentary sectional view illustrating delamination of the tape layer when the sheath is unrolled as it is applied to a wearer.

FIG. 10 is a side elevational view showing an alternate step in a second embodiment of the procedure that may be substituted for the steps depicted in FIGS. 2 and 4.

FIG. 11 is an enlarged fragmentary sectional view taken along line 11—11 of FIG. 10.

DETAILED DESCRIPTION OF PREFERRED EMBODIMENTS

Figure 1:
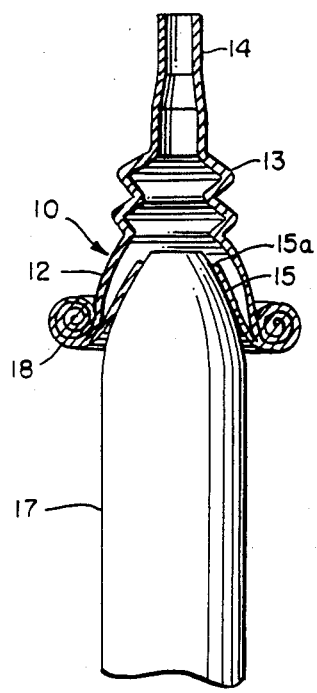
FIG. 1 is a sectional view illustrating a late stage in the manufacture of a catheter sheath where the sheath is supported in rolled condition upon the end of a mandrel.

Referring to FIGS. 1-7 of the drawings, the numeral 10 generally designates an elastic condom-type sheath particularly suitable for use as the external catheter in a male urinary collection system. The sheath is similar in construction to the sheath disclosed in co-owned patents 4,581,026, 4,626,250, and 4,589,974, the disclosures of which are incorporated by reference herein. The sheath is formed of latex rubber or other thin, highly-stretchable, elastic material and includes an elongated cylindrical body portion or member 11 (FIG. 4), a tapered neck portion 12 that may have concentric convolutions or enlargements 13 at its distal end, and a drainage tube portion 14 to which a suitable drainage tube (not shown) may be attached. In the preferred form of the invention, the sheath also includes an inner sleeve portion 15 which is disposed within the sheath's tapered neck portion 12. The sleeve merges at its proximal end with the interior of the sheath at the junction of cylindrical body portion 11 and neck portion 12, and terminates in a distal opening 15a spaced from the reduced end of the neck portion 12. The purpose of the inner sleeve is to produce a snug, fluid-tight, protective covering over the glans of the penis when the device is worn, thereby protecting the glans against prolonged contact with small amounts of residual urine that may remain within the sheath's neck portion. While experience has shown that the inclusion of an inner sleeve in such a catheter sheath is highly advantageous, it is to be understood that substantial benefits may be achieved by the method and construction of the present invention even if the sleeve were omitted.

In performing the method of this invention, a catheter sheath 10 is first supported upon a mandrel 17 as depicted in FIG. 1. The mandrel may be formed of aluminum, rigid plastic, or any other suitable material, and functions primarily as a supporting device for final steps in the manufacture of the catheter sheath. It will be observed that the cylindrical body portion of the catheter is in rolled condition, such portion having been rolled outwardly upon itself to form a single torus 18 having successively larger rolls or turns (FIGS. 1, 7).

Figure 2:
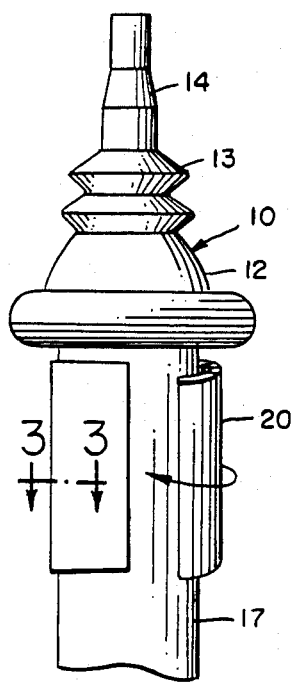
FIG. 2 is a fragmentary side elevational view depicting a subsequent step in which a tape laminate is wrapped about the mandrel directly below the rolled catheter sheath.
Figure 3:
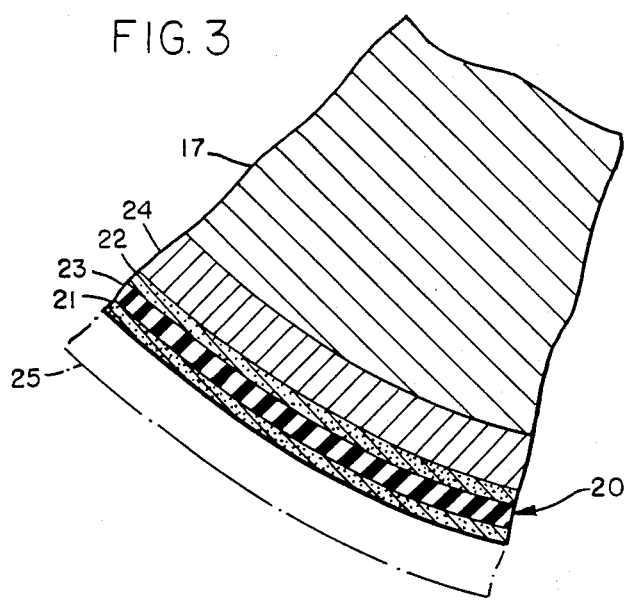
FIG. 3 is a greatly enlarged fragmentary sectional view taken along line 3—3 of FIG. 2.

FIG. 2 shows a section of tape 20 being wrapped about mandrel 17 directly below sheath 10. The tape is a laminate with its multiple layers being shown clearly in the enlarged horizontal sectional view of FIG. 3. Specifically, the tape includes a first adhesive layer 21, a second adhesive layer 22, and an elastomeric core layer 23 interposed between the adhesive layers. The tape may also include a backing release layer 24 formed for example, of silicone-coated paper or plastic material. A second protective layer 25 may also be provided of the same or similar composition as layer 24; however, since omission of layer 25 is believed preferable, especially in automated operations, that layer is shown only in phantom in FIG. 3.

The first adhesive layer 21 and the second adhesive layer 22 may be composed of the same or different adhesives. Any suitable pressure-sensitive adhesives may be used. Acrylic-based, medical-grade, pressure-sensitive adhesives are believed particularly suitable, especially for the first adhesive layer 21 which, in use of the product, will come into direct contact with the wearer's skin.

The elastomeric core layer 23 may be a homogeneous composition of silicone rubber or any other suitable highly-stretchable elastomer. The thin elastomeric layer should be non-porous and its affinity for the first adhesive layer 21 should be less than for the second adhesive layer 22. Such differences in adhesion forces may be achieved by controlling the composition of the elastomeric core layer, or the compositions of the two adhesive layers, or both. Thus, the elastomeric core layer may itself be a sub-laminate so that its opposite faces adhere with different degrees of adhesion to the pressure-sensitive adhesive (or adhesives) of layers 21 and 22. As an example, the elastomeric core layer may be formed of an elastoplastic such as Kraton (a block copolymer composed of polystyrene segments in a matrix of polybutadiene or polyisoprene manufactured by Shell Chemical Company, Houston, Texas) with a thin release coating of silicone on its face that contacts the first adhesive layer 21. The elastomeric core layer 23 will therefore cling far more tenaciously to the second adhesive layer 22 than to the first adhesive layer 21. Alternatively, as already indicated, the differences in the forces of adhesion on opposite sides of the elastomeric core layer may be achieved by adjusting the compositions of adhesive layers 21 and 22, in which case the elastomeric core layer may either be a sub-laminate or a single homogeneous material as shown.

It is essential that the affinity or strength of adhesive attachment between the first adhesive layer 21 and the elastomeric core layer 23 be less than the strength of adhesive attachment between each of the adhesive layers and the surfaces of sheath 10. As a result, when the sheath 10 and the elastomeric and adhesive layers of the laminate 20 are rolled together into a torus as described hereinafter, and then subsequently unrolled, a delamination of the tape will occur with the elastomeric layer 23 and second adhesive layer 22 remaining on the outside of the sheath and the first adhesive layer 21 clinging to the sheath's inner surface.

Figure 4:
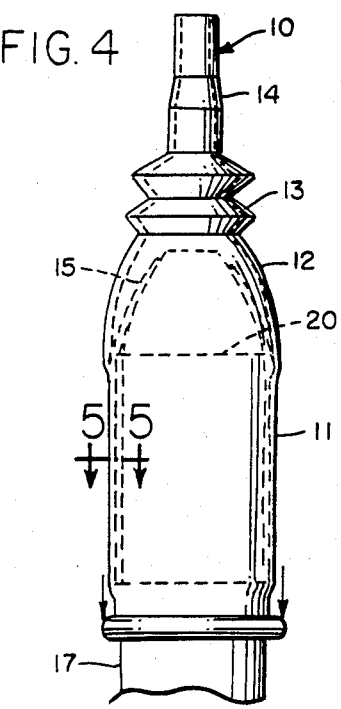
FIG. 4 is a side elevational view similar to FIG. 2 but showing a subsequent step in which the sheath is partially unrolled over the mandrel and the tape supported by it.

Referring to FIGS. 2 and 4, after the tape laminate 20 and paper release sheet 24 are wrapped about mandrel 17, sheath 10 is unrolled over the exposed surface of the first adhesive layer 21 (FIG. 4). In cross section, the layers then appear as shown in FIG. 5. When the sheath is re-rolled as depicted in FIG. 6, the release sheet 24 remains in place about the mandrel but the tape laminate composed of the first and second adhesive layers 21 and 22, and the elastomeric layer 23 sandwiched therebetween, transfers from the release sheet 24 to sheath 10. This occurs because the adhesive forces between each of the layers of the tape, and between the tape and sheath 10, are greater than the forces of attraction between the laminate and release sheet 24. The final result is the completed sheath 10 depicted in FIG. 7 with the tape laminate 20 disposed between successive layers or rolls of the rolled cylindrical body portion 11 of the sheath.

FIG. 8 shows a segment of the rolled body portion with only two successive turns of the sheath, and the laminate disposed between them, depicted in solid lines for clarity of illustration. In use of the product, the rolled sheath is brought into contact with the glans of the penis and the cylindrical body of the sheath is unrolled. As it is unrolled, adhesive layer 21 clings to the inner surface 10a of the sheath 10 whereas the second adhesive layer 22 firmly adheres to the sheath's outer surface 10b(FIG. 9). A peeling action occurs, with the tape laminate 20 separating or delaminating at the junction of the first adhesive layer 21 and elastomeric core layer 23.

The outer surface of the elastomeric core layer 23 therefore functions as a release surface that promotes delamination of the tape 20 when the sheath is unrolled at the time of application. Such outer surface is smooth and non-tacky. Since the core layer 23 is imperforate, tough, and elastic, that layer also tends to reinforce the sheath and provide increased protection against pinholes and their formation. Such reinforcement is considered desirable in all sheath constructions but is particularly beneficial where the sheath is provided with an inner sleeve 15 as shown in the drawings. Under such circumstances, the elastomer not only reinforces the cylindrical portion of the sheath to block the development of pinholes but, where the elastomeric core layer extends beyond the zone of merger between the inner sleeve 15 and the body 11 of the sheath, the elastomeric layer effectively reinforces that zone.

FIGS. 10 and 11 illustrate a method and construction similar to the one already described except that the laminate 20' is adhesively affixed to the outer surface 10a of sheath 10 (FIG. 10) rather than to its inner surface (FIGS. 2, 4). For that purpose, the paper release layer 24 used in the first embodiment is omitted and the second adhesive layer 22' of tape laminate 20' is brought into direct adhesive contact with the outer surface 10b of the sheath when the tape is wrapped about that sheath (FIGS. 10, 11). If desired, a protective release layer 25' may be used to protect the first adhesive layer 21' as the tape is drawn about sheath 10 although, as described in conjunction with the preceding embodiment, the protective layer may be omitted, particularly in automated operations. The compositions of the first and second adhesive layers 21' and 22' respectively, and of the elastomeric layer 23', are identical to those of layers 21-23, respectively, of the first embodiment. Also, the remaining steps in the manufacture of the catheter sheath are essentially the same as depicted in FIGS. 6-9. The catheter sheath is rolled upon the mandrel to form a product having the same construction and appearance as shown in FIG. 7. During such rolling operation, the first adhesive layer 21' is brought into contact with the inner surface 10a of the sheath so that during subsequent unrolling of the catheter sheath, at the time of application to a wearer, the tape laminate 20' will peel apart and the first adhesive layer 21' will alone remain along the sheath's inner surface to provide adhesive attachment between that sheath and the wearer.

While in the foregoing we have disclosed embodiments of the invention in considerable detail for purposes of illustration, it will be understood by those skilled in the art that many of these details may be varied without departing from the spirit and scope of the invention.

We claim:

1. A sheath for a condom catheter, said sheath comprising a thin, flexible cylindrical member of elastic material having inner and outer surfaces and being rolled outwardly upon itself to form a torus having successively larger turns; and a thin, flexible, delaminateable tape means interposed between successive turns of said rolled torus and having multiple layers adhering to each other; said layers comprising a first adhesive layer, a second adhesive layer, and a highly-stretchable elastomeric layer disposed between said first and second adhesive layers and having a smooth, non-tacky outer surface; said first adhesive layer being adhered to said inner surface of said member and said second adhesive layer being adhered to said outer surface of said member; said elastomeric layer being adhered more securely to said second adhesive layer than to said first adhesive layer and said first adhesive layer having less affinity for said elastomeric layer than each of said adhesive layers has for the surfaces of said member; said tape means undergoing delamination with said first adhesive layer remaining upon the sheath's inner surface for securing the sheath to a wearer and said second adhesive layer, covered by said elastomeric layer, remaining on the sheath's outer surface, when said sheath is unrolled over a wearer's penis.

2. The sheath of claim 1 in which said elastomeric layer is homogeneous.

3. The sheath of claim 1 in which said elastomeric layer is provided with a coating of release material in contact with said first adhesive layer.

4. The sheath of claim 1 in which said elastomeric layer is imperforate.

* * * * *